US006823215B2

United States Patent
Obel et al.

(10) Patent No.: US 6,823,215 B2
(45) Date of Patent: Nov. 23, 2004

(54) IMPLANTABLE HEART STIMULATOR WITH MICROINSTABILITY TESTING FOR ELECTRODE CONTACT WITH TISSUE

(75) Inventors: Martin Obel, Danderyd (SE); Berit Larsson, Danderyd (SE)

(73) Assignee: St. Jude Medical AB, Järfälla (SE)

( * ) Notice: Subject to any disclaimer, the term of this patent is extended or adjusted under 35 U.S.C. 154(b) by 193 days.

(21) Appl. No.: 10/239,969

(22) PCT Filed: Mar. 28, 2001

(86) PCT No.: PCT/SE01/00679

§ 371 (c)(1),
(2), (4) Date: Sep. 25, 2002

(87) PCT Pub. No.: WO01/74439

PCT Pub. Date: Oct. 11, 2001

(65) Prior Publication Data

US 2003/0078626 A1 Apr. 24, 2003

(30) Foreign Application Priority Data

Mar. 29, 2000 (SE) .............................................. 0001112

(51) Int. Cl.[7] .............................................. A61N 1/362
(52) U.S. Cl. ...................................................... 607/27
(58) Field of Search ............................ 607/9, 11, 25, 607/27, 28

(56) References Cited

U.S. PATENT DOCUMENTS

| | | | | |
|---|---|---|---|---|
| 5,265,603 A | * | 11/1993 | Hudrlik | ........................ 607/9 |
| 5,476,487 A | | 12/1995 | Sholder | |
| 5,836,990 A | | 11/1998 | Li | |
| 5,935,079 A | | 8/1999 | Swanson et al. | |
| 6,317,633 B1 | * | 11/2001 | Jorgenson et al. | ............ 607/28 |
| 6,553,259 B2 | * | 4/2003 | Mouchawar et al. | .......... 607/11 |

* cited by examiner

*Primary Examiner*—George Manuel
(74) *Attorney, Agent, or Firm*—Schiff Hardin LLP

(57) ABSTRACT

An implantable heart stimulator has a control and detection circuit which operates a pulse generator which emits stimulation pulses which are delivered to cardiac tissue via at least one electrode lead adapted for insertion in the heart of a patient. The electrode lead has an electrode surface which is intended to be in contact with heart tissue. The control and detection circuit performs a microinstability test by causing the pulse generator to emit a predetermined number of stimulation pulses, each having the same stimulation energy. The control and detection circuit determines a microinstability test value, representing a measure of the contact between the electrode surface and the heart tissue, as a ratio of a number of stimulation pulses, within said predetermined number of stimulation pulses, for which capture is detected, and the predetermined number of stimulation pulses.

12 Claims, 1 Drawing Sheet

IMPLANTABLE HEART STIMULATOR WITH MICROINSTABILITY TESTING FOR ELECTRODE CONTACT WITH TISSUE

BACKGROUND OF THE INVENTION

1. Field of the Invention

The present invention relates to an implantable heart stimulator.

2. Description of the Prior Art

Immediately after implantation of a heart stimulator and insertion of a heart electrode lead into the heart and attachment of a stimulation electrode carried by the head to heart tissue, the stimulation threshold, i.e. the least energy (pulse amplitude if the pulse width is constant) required to achieve heart contraction, is relatively high. After the first months following implantation of a heart stimulator the stimulation threshold eventually stabilizes at a more or less constant value in the order of some Volts (2–5 Volts).

Natural fluctuations of the stimulation threshold occur due to e.g. the activity of the patient (awake or asleep), the intake of drugs, etc. These fluctuations might be considered as more or less predictable.

Another type of fluctuation, which is considered more unpredictable, might occur when the electrode surface of the electrode lead is not in good contact with heart tissue.

U.S. Pat. No. 5,836,990 discloses a method and apparatus for determining electrode/tissue contact. The contact between an electrophysiology catheter electrode and cardiac tissue covered by blood is sensed by applying a constant voltage or current square wave signal to the electrode and then monitoring the voltage or impedance or current at the electrode before, during and after the electrode contacts the tissue. In the apparatus disclosed in U.S. Pat. No. 5,836,990 a dedicated signal is applied to the cardiac tissue in order to determine an electric parameter related to the contact between the electrode and the cardiac tissue. The electric parameter is then monitored and the contact is determined.

A drawback with the apparatus disclosed in the above patent is that it requires dedicated circuitry in order to determine the degree of contact between the electrode and the cardiac tissue.

SUMMARY OF THE INVENTION

An object of the present invention is to provide an improved implantable heart stimulator that avoids the above mentioned drawbacks with the apparatus disclosed in U.S. Pat. No. 5,836,990 and that identifies varying stimulation thresholds due to microinstability.

Microinstability is as a term used to describe how stable the electrode surface, e.g. the electrode tip, is attached to the heart tissue. If the electrode surface not is properly attached to the heart tissue, movements of the electrode might result in varying stimulation thresholds dependent on varying electrical conditions around the electrode. This in turn might result in more frequent delivery of back-up pulses which can be both unpleasant for the patient and reduce the battery capacity of the heart stimulator.

The object of the present invention thus is achieved by performing a microinstability test in order to identify varying stimulation thresholds and to increase the stimulation energy if so required to eliminate the influence of the varying threshold.

It is a further object of the invention to perform, in addition to a stimulation threshold search, a microinstability test in order to be able to adjust the stimulation energy to a level at which the effects of microinstability are reduced or eliminated.

DESCRIPTION OF THE PREFERRED EMBODIMENTS

Figure 1:
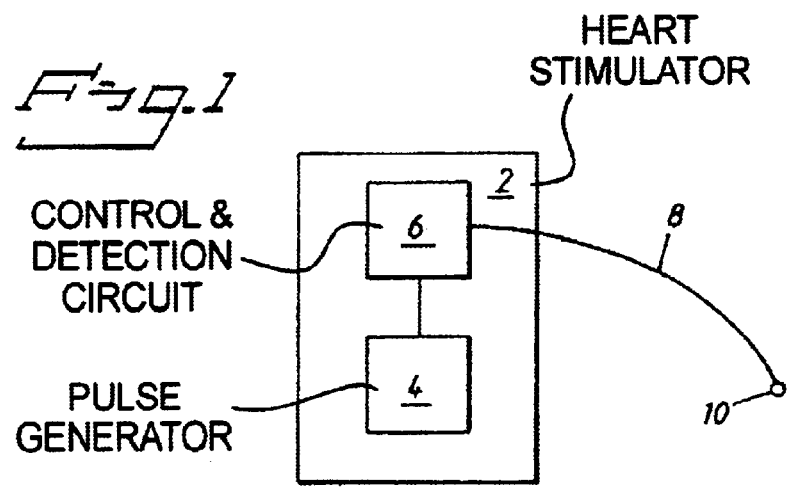
FIG. 1 shows a block diagram of the heart stimulator according to the present invention.

FIG. 1 shows an implantable heart stimulator 2 according to the invention, having a control and detection unit 4, a pulse generator 6 which generates stimulation pulses that are delivered to a heart via at least one electrode lead 8 that is adapted for insertion into the heart of a patient. The electrode lead 8 is provided with an electrode surface 10 intended to be in contact with heart tissue. The electrode surface 10 is conventionally often arranged as a tip electrode but the invention is equally applicable for any electrode surface intended to be in contact with heart tissue, e.g. different kinds of ring electrodes.

The heart stimulator naturally also has an energy source and other components not further described herein as they have no significance for the present invention.

A microinstability test may be performed in many different ways.

According to a preferred embodiment of the invention a microinstability test is performed directly after a stimulation threshold search has been performed.

According to an alternative embodiment of the invention is the microinstability test performed at regular intervals independently of any threshold search. The microinstability test also may be performed in relation to a heart stimulator not provided with threshold search circuitry. The test need not be initiated at regular intervals but instead can be initiated on demand, e.g. in response to an external signal, e.g. a magnetic signal, or in response to a sensing circuit detecting the occurrence of some specified event, e.g. if the threshold is varying irregularly.

The microinstability test is performed by the control and detection unit 4 (including e.g. a microprocessor) which supplies a control signal to the pulse generator 6 to cause the pulse generator 6 to generate a predetermined number of stimulation pulses to the heart tissue via the electrode lead 8 and which also detects capture, if any, for each of these stimulation pulses. The number of generated stimulation pulses is e.g. in the interval 10–20, preferably 15. All stimulation pulses during the microinstability test have the same stimulation energy. A typical stimulation pulse has an amplitude of some volts and a pulse width of 0.01 to 1.0 ms. A measure of the quality of the contact between the electrode surface 10 and heart tissue is provided by a microinstability test value. This value is determined by the control and detection unit 4 in accordance with an algorithm, as the ratio between the number of stimulation pulses of the predetermined number that resulted in capture, and the predetermined number. If one or more losses of capture are observed during the microinstability test, the test value is less than 1. The microinstability test is then repeated with slightly higher stimulation amplitude, typically 0.25 V, until 100% capture is obtained during the microinstability test.

According to a further refinement of the invention is the microinstability test is performed with a shortened relevant stimulation interval, e.g. AV-interval or VV-interval, to ensure that only stimulated heart events occur during the test. The interval is shortened with a predetermined time in the order of 5–100 ms.

According to a preferred embodiment of the invention and as indicated above the microinstability test is performed after a stimulation threshold search has been completed. In order to fully explain the advantages of the present invention a threshold search algorithm is illustrated in FIG. 2.

Figure 2:
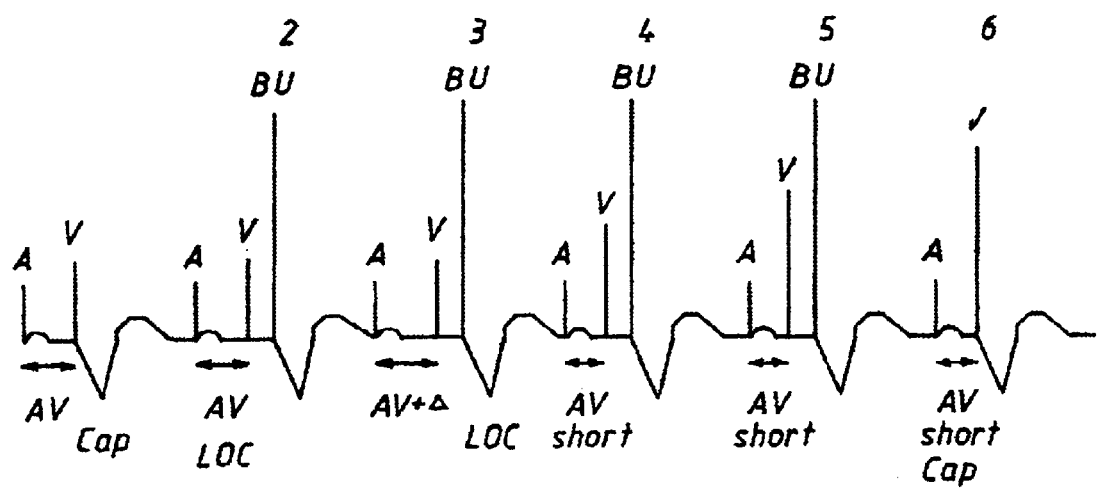
FIG. 2 is an IEGM illustrating the principles of a threshold search algorithm for use in the present invention.

FIG. 2 shows an IEGM illustrating the principles of threshold search algorithms according to established standard prior art, see e.g. U.S. Pat. No. 5,476,487, and applicable in relation with the present invention. A and V designate atrial and ventricular stimulation pulses, respectively. BU is a high output backup pulse delivered if loss of capture (LOC) occurs. As can be seen (complex 3) the preprogrammed AV-interval is prolonged by Δ when a LOC occurs (complex 2). The reason for that is to await any intrinsic event if the first LOC was the result of a fusion beat. In this case there is no intrinsic activity and the LOC was not a result of a fusion beat but was due to a changed stimulation threshold of the heart tissue, and a stimulation threshold search is initiated.

In FIG. 2 during the threshold search the pre-programmed AV-interval is shortened to "AV-short" to override any intrinsic heart activity. The ventricular stimulation amplitude is successively stepped up by a predetermined amplitude step of e.g. 0.1–0.3 V and each unsuccessful ventricular stimulation pulse is followed by a back-up pulse. As an alternative the ventricular stimulation amplitude may start at an amplitude above the stimulation threshold and then successively be stepped down until non-capture occurs. This is performed until the stimulation threshold is detected, i.e. capture is detected from the ventricular stimulation pulse, and the stimulation pulse amplitude is then set to a value that equals the stimulation threshold plus a working margin, e.g. 0.3 V.

It should be noted that the threshold search, according to the established technique disclosed in the above-mentioned U.S. Pat. No. 5,476,487, is performed by using a pre-programmed AVI shortened to "AVI-short" as indicated above.

The microinstability test is then performed for a predetermined number of heart cycles, typically 15, with the shortened AVI used in the threshold search using the measured threshold as stimulation amplitude. If no loss of capture is observed during the predetermined number of heart cycles then the previously determined threshold is valid. If one or more losses of capture are observed then the microinstability test is repeated with a slightly higher stimulation amplitude, typically 0.25 V. The test is repeated until 100% capture is obtained during the microinstability test. The new stimulation amplitude valid for the period until the next threshold search is obtained after adding a working margin to the amplitude.

The present invention is not limited to the above-described preferred embodiments. Various alternatives, modifications and equivalents may be used. Therefore, the above embodiments should not be taken as limiting the scope of the invention, which is defined by the appended claims.

Although modifications and changes may be suggested by those skilled in the art, it is the invention of the inventors to embody within the patent warranted heron all changes and modifications as reasonably and properly come within the scope of their contribution to the art.

What is claimed is:

1. An implantable heart stimulator comprising:
a pulse generator which generates stimulation pulses;
an electrode lead connected to said pulse generator having an electrode with an electrode surface, and being adapted for insertion into a heart with said electrode surface adapted for contact with tissue in said heart;
a control and detection circuit connected to said pulse generator and to said electrode lead for controlling generation of said stimulation pulses by said pulse generator and for, via said electrode lead, detecting capture; and
said control and detection circuit conducting a microinstability test during which said control and detection circuit causes said pulse generator to emit a predetermined number of stimulation pulses having identical stimulation energy, and wherein said control and detection circuit determines a microinstability test value, representing a measure of said contact between said electrode surface and said tissue, as a ratio between a number of said predetermined number of stimulation pulses for which capture is detected, and said predetermined number.

2. An implantable heart stimulator as claimed in claim 1 wherein said control and detection circuit repeats said microinstability test by causing said pulse generator to emit said predetermined number of stimulation pulses with a higher stimulation amplitude, if at least one absence of capture is detected during said microinstability test, until 100% capture is detected during said microinstability test.

3. An implantable heart stimulator as claimed in claim 2 wherein said control and detection circuit causes said pulse generator to emit said predetermined number of stimulation pulses, each time said microinstability test is repeated, with a stimulation amplitude that is higher by 0.25 V than the stimulation amplitude in an immediately preceding microinstability test.

4. An implantable heart stimulator as claimed in claim 1 wherein said control and detection circuit causes said pulse generator to emit said predetermined number of stimulation pulses in said microinstability test in a range between 10 and 20 stimulation pulses.

5. An implantable heart stimulator as claimed in claim 1 wherein said control and detection circuit causes said pulse generator to emit 15 stimulation pulses, as said predetermined number of stimulation pulses, in said microinstability test.

6. An implantable heart stimulator as claimed in claim 1 wherein said control and detection circuit further initiates a stimulation threshold search, and initiates said microinstability test after said stimulation threshold search.

7. An implantable heart stimulator as claimed in claim 1 wherein said control and detection circuit causes said pulse generator to emit said stimulation pulses, outside of said microinstability test, with a stimulation interval, and causes said pulse generator to emit said predetermined number of stimulation pulses in said microinstability test with said stimulation interval being shortened by a predetermined time.

8. An implantable heart stimulator as claimed in claim 7 wherein said stimulation interval is a AB-interval.

9. An implantable heart stimulator as claimed in claim 7 wherein said stimulation interval is VV-interval.

10. An implantable heart stimulator as claimed in claim 7 wherein said predetermined time is in a range between 5 and 100 ms.

11. An implantable heart stimulator as claimed in claim 1 wherein said control and detection circuit initiates said microinstability test at regular intervals.

12. An implantable heart stimulator as claimed in claim 11 wherein said control and detection circuit initiates said microinstability test every 8 hours.

* * * * *